United States Patent [19]
Shen et al.

[11] Patent Number: 5,883,244
[45] Date of Patent: Mar. 16, 1999

[54] LYTIC β-1,3-GLUCANASE GENE

[75] Inventors: Shi-Hsiang Shen, Beaconsfield; Pierre Chretien, Montreal; Lison Bastien, Vaudreuil; Steve N. Slilaty, Ville St-Laurent, all of Canada

[73] Assignee: Her Majesty the Queen in right of Canada, as represented by the National Research Council of Canada, Ottawa, Canada

[21] Appl. No.: 82,909

[22] Filed: Jun. 29, 1993

Related U.S. Application Data

[63] Continuation of Ser. No. 568,869, Aug. 17, 1990, abandoned.

[51] Int. Cl.$^6$ .......................... C12N 15/56; C12N 15/67; C12N 15/70; C12N 9/24
[52] U.S. Cl. ...................... 536/23.2; 536/23.4; 435/200; 435/69.1; 435/252.33; 435/320.1; 935/14; 935/41; 935/73
[58] Field of Search .................................. 435/200, 209; 536/23.2, 24.1, 23.4

[56] References Cited

U.S. PATENT DOCUMENTS 5,094,951  3/1992  Rosenberg ............................. 435/190

FOREIGN PATENT DOCUMENTS

| | | |
|---|---|---|
| 8654937 | 9/1986 | Australia . |
| 8939078 | 2/1990 | Australia . |
| 100254 | 2/1984 | European Pat. Off. . |
| 137280 | 4/1985 | European Pat. Off. . |
| 251744 | 1/1988 | European Pat. Off. . |
| 226012 | 8/1985 | German Dem. Rep. . |
| 269166 | 6/1989 | German Dem. Rep. . |
| 272102 | 9/1989 | German Dem. Rep. . |
| 61-040792 | 2/1986 | Japan . |
| 62-205785 | 9/1987 | Japan . |
| 1252292 | 10/1989 | Japan . |
| 8701388 | 3/1987 | WIPO . |
| 9000609 | 1/1990 | WIPO . |

OTHER PUBLICATIONS

Shen et al., "Primary Sequence of the Glucanase Gene from *Oerskovia xanthineolytica*", The Jnl. of Biological Chem., 266: 1058–1063 (1991).

Whitcombe, "Molecular Cloning and Analysis of a β–1, 3–Glucanase . . .", Dissertation submitted to the University of Leicester (1988).

Borriss, Rainer et al., Expression in *Escherichia coli* of a cloned beta–glucanase gene from *Bacillus amyloliquefaciens*, Appl. Microbiol. Biotechnol., (1985) 22:63–71.

Fuller, Forrest, A family of cloning vectors containing the lacUV5 promoter, Gene 19 (1982), 43–54.

Studier, F. William and Moffatt, Barbara A., Use of bacteriophage T7 RNA polymerase to direct selective high–level expression of cloned genes, J. Mol. Biol. (1986), 189, 113–130.

Schwarz, W.H., et al., 1988, Biotechnology Letters 10(4):225–230.

(List continued on next page.)

*Primary Examiner*—Robert A. Wax
*Assistant Examiner*—William W. Moore
*Attorney, Agent, or Firm*—Foley & Lardner

[57] ABSTRACT

The present invention relates to recombinant β-1,3-glucanase essentially free of proteases. The enzyme is obtained through the use of a recombinant DNA expression vector which comprises a DNA sequence encoding the β-1,3-glucanase gene or mutants and variants thereof placed under the control of an exogenous expression promoter, preferably a bacterial promoter. Also, the β-1,3-glucanase gene may include sequences flanking the open reading frame of the native β-1,3-glucanase gene. The present invention also relates to a microorganism transformed with a recombinant DNA expression vector comprising the β-1,3-glucanase gene or mutants and variants thereof under the control of an exogenous expression promoter.

2 Claims, 8 Drawing Sheets

OTHER PUBLICATIONS

Doi, K., et al., 1976, Agricultural and Biological Chemistry, 40(7): 1355–1362.

Scott, J.A. and R. Schekman, 1980, Journal of Bacteriology 142(2): 414–423.

Béguin, P., et al., 1985, Journal of Bacteriology, 162(1): 102–105.

Svensson, B., et al., 1986, European Journal of Biochemistry, 154:497–502.

Doi, K. and A. Doi, 1986, Journal of Bacteriology, 168(3): 1272–1276.

Whitcombe, D.M., 1988, Dissertation, University of Leicester, 144 pages, Abstract in Dissertation Abstracts Int'l. 51/04(B): 1809.

Watanabe, T., et al., 1989, Agricultural and Biological Chemistry, 53(7): 1759–1767.

Yahata, N., et al., 1990, Gene, 86(1): 113–117.

Nagata, S. et al., 1990, Agricultural and Biological Chemistry 54(10):2675–2680.

Innis, M.A., et al., 1988, Proceedings of the National Academy of Sciences, USA, 85: 9436–9440.

Forsmon, M., et al., 1990, Journal of General Microbiology 136: 589–598.

Ohama, T., et al., 1987, Journal of Bacteriology 149(10): 4770–4777.

Mizasawa, S., et al., 1986, Nucleic Acids Research 14(3): 1319–1324.

De Boer, H.A., et al., 1983, in *Genes: Structure and Expression*, Kroon, A.M., Ed., John Wiley & Sons Ltd, publishers, pp. 205–248.

```
                                                                                            1092
GACGGGCAGGTCCTCAGCACGGGCATGCTCAAGCCGAACGGCTACGAGGCCTTCTACACGGCCCTCGAGGGCGCGGGTGGGC
 D  G  Q  V  L  S  T  G  M  L  K  P  N  G  Y  E  A  F  Y  T  A  L  E  G  A  G  W  G
169                        197
                                                                                            1176
GGGCTCGTGCAGCGCGCCCCGGACGGGAGCCGCCTGCGCGCTCAACCCGTCGCACGGGATCGACGTCGGGAAGATCTCGTCG
 G  L  V  Q  R  A  P  D  G  S  R  L  R  A  N  P  S  H  G  I  D  V  G  K  I  S  S
              225
                                                                                            1260
GCCTCGATGACTCCTACGTCACCGAGGTGTGGAACTCGTACCGCGACATGGTCGTCACGCCGTTCTCCCACGAGCCC
 A  S  I  D  S  Y  V  T  E  V  W  N  S  Y  R  D  M  V  V  T  P  F  S  H  E  P
          253
                                                                                            1344
GGCACGCAGTTCCGGGGCCGGGTCGACGGCGGTTCCGGCTTCAGGAGCGGGTCCGGCCAGGAGGTCGCCGCGTTCAAGAAG
 G  T  Q  F  R  G  R  V  D  G  G  D  W  F  R  R  F  R  S  G  S  G  Q  E  V  A  A  F  K  K
              281
                                                                                            1428
CCCGACGCGTCGAGCGTGTACGGGTGCCACAAGGACCTCGCCCCAAACGACCACGTCGTGGGCCCGATCGCCCGCACCCTG
 P  D  A  S  S  V  Y  G  C  H  K  D  L  A  P  N  D  H  V  V  G  P  I  A  R  T  L
                      309
                                                                                            1512
TGCGCCGCGCTCGTGCGCACGGCGCTGACGCCGAACAACCCGGACGCGAACAGCGCCGGCTTCTACCAGGACGCGGCGCGC
 C  A  A  L  V  R  T  A  L  T  P  N  N  P  D  A  N  S  A  G  F  Y  Q  D  A  R
                              337
                                                                                            1596
ACCAACGTCTACGCGAAGCTCGCCCACCAGCAGATGGCCAACGGCAAGGCGTACGCGTTCGACTTCGACGACGTCGGCGCAC
 T  N  V  Y  A  K  L  A  H  Q  Q  M  A  N  G  K  A  Y  A  F  D  F  D  D  V  G  A  H
                                      365
                                                                                            1680
GAGTCGCTCGTGCACGACGGCCCCTACCAGGCCGCAGCGTACATCAAGCTCGACCCGTTCACCGGCACCGCCCCTCTGGGAAC
 E  S  L  V  H  D  G  P  Y  Q  A  A  A  Y  I  K  L  D  P  F  T  G  T  A  T  P  L  G  N
                                              393
                                                                                            1764
GGGGCAGCACCGAGCAGCCCGGCGGGACGCCGGGAGGCACGCCGGGAGGTCCGGGACTGCCGGCTGGAGCGCTCGACCCTCTGCCTC
 G  G  S  T  E  Q  P  G  G  T  P  G  G  L  P  A  G  A  L  R  I  G  S  T  L  C  L
                                                      421
                                                                                            1848
GACGTCCCGTGGGCCGACCCGACCGACACCAACCAGGTCCAGCTCGCCAGCGGCAACGCCGCAGCAGTGACGCGC
 D  V  P  W  A  D  P  T  D  T  N  Q  V  Q  L  A  T  C  S  G  N  A  A  Q  W  T  R
```

FIG. 2C

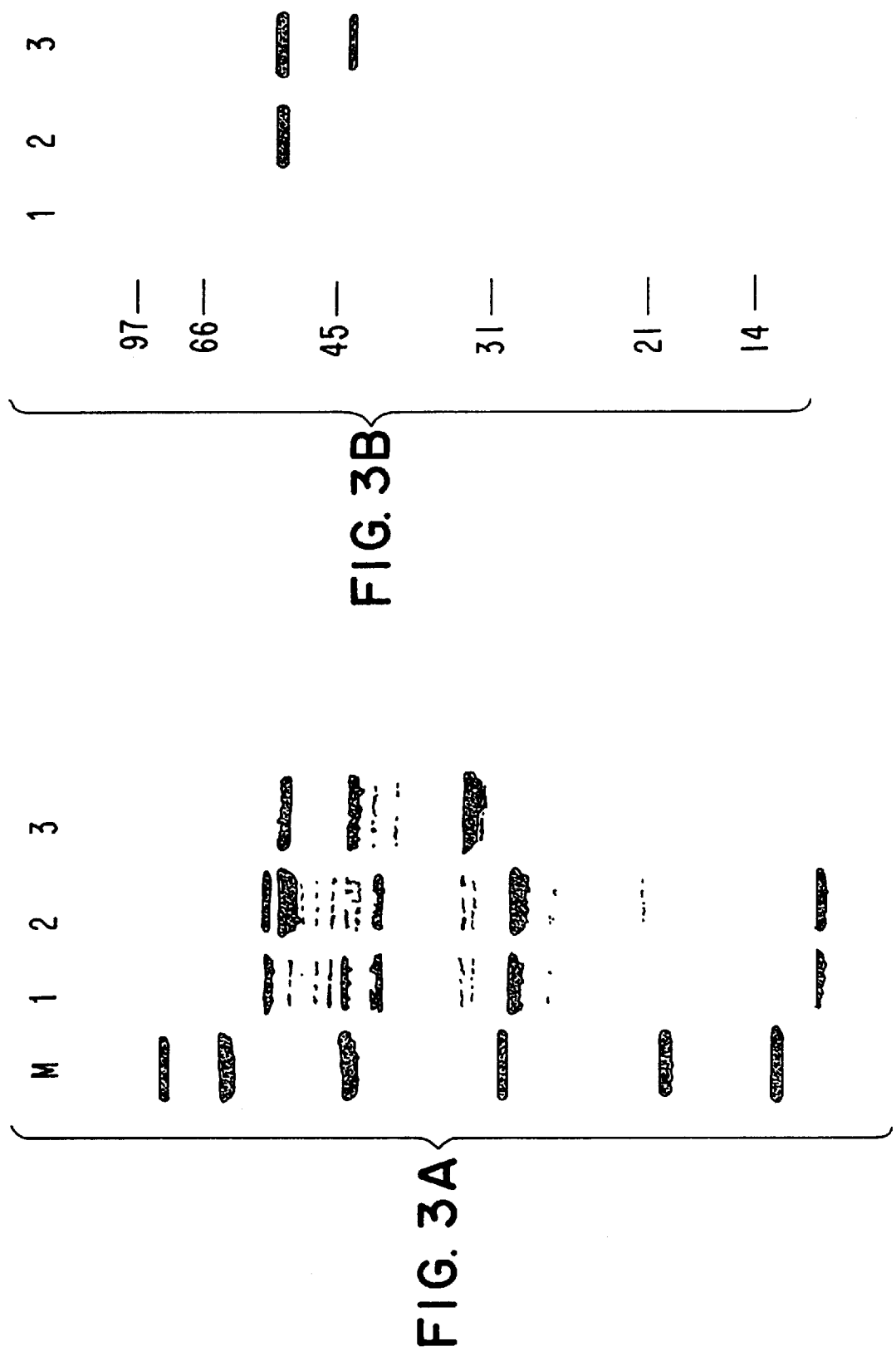

LYTIC β-1,3-GLUCANASE GENE

This application is a continuation of application Ser. No. 07/568,869, filed Aug. 17, 1990, now abandoned.

FIELD OF THE INVENTION

The present invention relates to the preparation of recombinant β-1,3-glucanase enzyme essentially free of proteases. The enzyme is obtained through the isolation, sequencing, and cloning of a β-1,3-glucanase gene. The gene is expressed in, and the protein is purified from, a heterologous microorganism transformed with a recombinant DNA vector containing the nucleotide sequence of the β-1,3-glucanase under the control of an exogenous promoter.

BACKGROUND OF THE INVENTION

The yeast cell wall is composed of glucan, mannoprotein and chitin. In most yeasts and especially Saccharomyces, the polysaccharide glucan is predominantly β-1,3-linked with some branching via β-1,6-linkages. Several microorganisms have been reported to produce extracellular enzymes capable of lysing viable yeast cells. Analysis of the constituents of these lytic enzyme preparations revealed the presence, among other activities, of a β-1,3-glucanase and a protease. When combined with a thiol reagent, β-1,3-glucanase alone was found to be responsible for the yeast cell lysis function.

Several molecular forms of β-1,3-glucanase have been identified in the culture supernatant of Arthrobacter species. While all of the observed molecular forms of the enzyme possessed hydrolytic activity towards β-glucans (glucanase activity), only some were found capable of inducing lysis of viable yeast cells (lytic activity). It is not clear whether all of these species of glucanase are different native enzymes with different substrate specificities or, that the species deficient in the lytic function are products of proteolytic degradation of a single native enzyme containing both glucanase and lytic activity. Furthermore, presently available enzyme preparations for use in the lysis of yeast cells are unsatisfactory because they contain undesirable protease activity. Hence, it would therefore be desirable to provide a means for high level expression of a β-1,3-glucanase gene in a heterologous host for subsequent purification of the enzyme without interference or copurification of the endogenous protease.

A single molecular species of β-1,3-glucanase with lytic activity has been substantially but not completely purified away from the protease by Scott et al. (1980), J. Bacteriol. 142, 414–423, from the culture supernatant of *Oerskovia xanthineolytica*. On the other hand, Doi et al. (1986), J. Bacteriol. 168, 1272–1276, have succeeded in cloning into *E. coli* of a DNA fragment encoding a β-1,3-glucanase activity taken from *Arthrobacter sp.* strain YCWD3. However, the level of β-1,3-glucanase expression in *E. coli* from this cloned DNA fragment was low, and since its nucleotide sequence and location of the glucanase gene are not known, improving the expression level is difficult to achieve. Thus, incomplete removal of the protease and poor expression yields render the above systems unsuitable for any significant production of useful glucanase preparations.

SUMMARY OF THE INVENTION

With the present invention, there are provided means to improve the production of β-1,3-glucanase in various microbial systems including *E. coli*. This has been achieved by sequencing a DNA fragment comprising a gene coding for β-1,3-glucanase from *Oerskovia xanthineolytica* and by successfully expressing it in a microbial system, preferably *E. coli*, under the control of a strong exogenous promoter, preferably the lacUV5 promoter. This system enabled rapid isolation and purification of large quantities of the desired glucanase enzyme.

The knowledge of the exact sequence of the gene and its flanking regions has allowed optimization of the expression yields by permitting placement of a strong promoter, preferably the lacUV5 promoter, at a specific location upstream of the coding sequence. The recombinant enzyme preparation thus produced is essentially free of protease activity, thereby solving the most serious drawback encountered with the use of presently available glucanase preparations.

Thus, in accordance with the present invention, there in provided a recombinant DNA expression vector which comprises a DNA sequence encoding the β-1,3-glucanase gene mutants and variants thereof, placed under the control of an exogenous expression promoter. Preferably, the β-1,3-glucanase gene is under the control of an *E. coli* promoter such as the lacUV5 promoter.

More preferably, optimal expression yields are obtained when the β-1,3-glucanase gene comprised in the recombinant DNA expression vector of the present invention includes all or portions of the sequences flanking the open reading frame of the native β-1,3-glucanase gene. For example, location of the lacUV5 promoter 165 base pairs upstream of the β-1,3-glucanase coding sequence allowed advantageous and very high β-1,3-glucanase expression yields.

Also within the scope of the present invention is a microbial strain transformed with a recombinant DNA expression vector comprising the β-1,3-glucanase gene or mutants and variants thereof, placed under the control of an exogenous expression promoter. Preferably, the microbial strain is an *E. coli* bacterial strain transformed with a recombinant DNA expression vector comprising a β-1,3-glucanase gene or mutants and variants thereof with or without all or portions of the flanking sequences of the open reading frame of the native gene, under the control of a bacterial promoter such as the lacUV5 promoter.

Also within the scope of the present invention is a recombinant enzyme preparation comprising essentially the enzyme β-1,3-glucanase or mutants and variants thereof, in substantially pure form. This enzyme preparation is further characterized in that it is essentially free of protease activity. The glucanase recombinant enzyme produced using the expression vector referred to above exhibits two distinct enzymatic activities, namely a glucanase activity and a lytic activity. As mentioned earlier, the glucanase activity allows the enzyme to hydrolyse β-glucans whereas the lytic activity provides the enzyme with the ability to induce lysis of viable yeast cells. It has been found that by deleting a portion of the sequence of the β-1,3-glucanase gene, it was possible to obtain a mutant enzyme having no lytic activity while maintaining full glucanase activity.

Thus, the present invention also relates to a recombinant DNA expression vector which comprises a DNA sequence encoding a mutant β-1,3-glucanase gene coding for the synthesis of a glucanase enzyme exhibiting only a glucanase activity. The mutant gene is placed under the control of an exogenous promoter, preferably a bacterial promoter such as the lacUV5 promoter.

Optimal expression yields are obtained when the mutant β-1,3-glucanase gene includes all or portions of the sequences flanking the open reading frame of the native β-1,3-glucanase gene.

The scope of the present invention will be more readily appreciated by referring to the following description.

IN THE DRAWINGS

FIG. 2A–2C represent the complete nucleotide sequence of the β-1,3-glucanase gene and its flanking regions.

FIG. 3A and 3B represent the characterization of the glucanase enzyme expressed in *E. coli* by SDS-PAGE and immunoblotting.

DETAILED DESCRIPTION OF THE INVENTION

Figure 1:
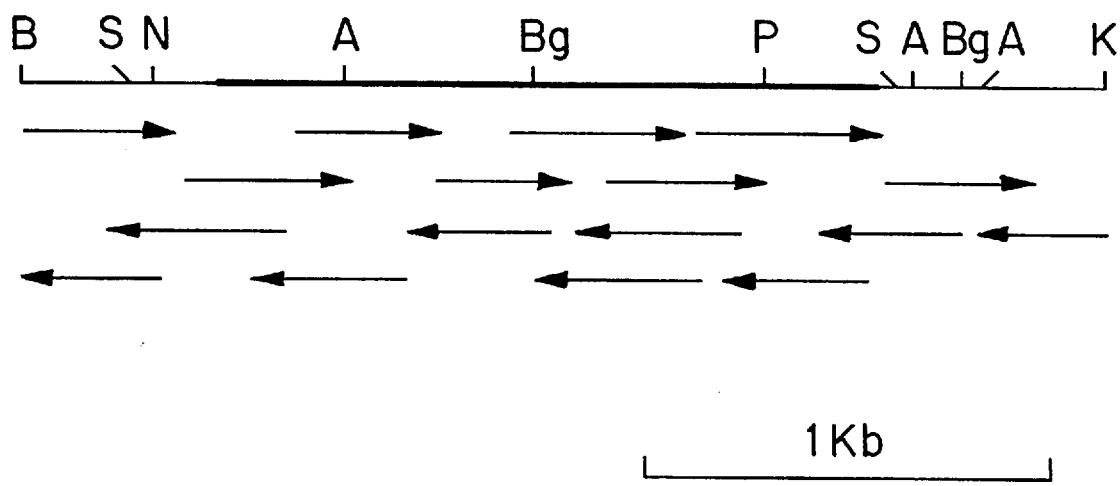
FIG. 1 represents the sequencing strategy used to obtain the nucleotide sequence of the β-1,3-glucanase gene along with a partial restriction map of the β-1,3-glucanase gene.

The present invention relates to a recombinant DNA expression vector useful for the transformation of a microbial strain which, as a result of this transformation, produces suitable amounts of the enzyme β-1,3-glucanase. The β-1, 3-glucanase gene from *Oerskovia xanthineolytica* has been cloned, sequenced, placed under the control of a strong exogenous promoter, preferably a bacterial promoter such as the lacUV5 promoter and subsequently inserted into a microbial strain, preferably a bacterial strain and more preferably *E. coli*.

The cloned gene has been successfully expressed in *E. coli*. The recombinant enzyme thus produced has been purified to near homogeneity and showed essentially no sign of protease activity. A significant increase in the expression level of the β-1,3-glucanase gene in *E. coli* was noted when the recombinant DNA expression vector of the present invention included the flanking sequences of the open reading frame of the native β-1,3-glucanase gene. In fact, a glucanase expression vector in which the lacUV5 promoter was fused directly upstream of the initiator ATG codon of the β-1,3-glucanase gene yielded 5 times less protein when compared with an expression vector comprising all or part of the flanking sequences of the native β-1,3-glucanase gene.

The present invention also relates to a microbial strain, preferably a bacterial strain, transformed to express a β-1, 3-glucanase gene under the control of an exogenous promoter, Preferably, the recombinant DNA expression vector containing the β-1,3-glucanase gene used to transform the bacterial strain includes the sequences flanking the open reading frame of the native gene and is placed under the control of the lacUV5 promoter.

The preferred embodiment of the present invention that is described hereinbelow relates to the use of the cloned and sequenced β-1,3-glucanase gene from *Oerskovia xanthineolytica* as a suitable means to achieve the objects of the present invention, that is to provide an expression vector through which the efficient production of considerable quantities of substantially pure glucanase enzyme can be achieved. However, it is to be appreciated that the present invention is not limited to the β-1,3-glucanase gene of *Oerskovia xanthineolytica*. Other experiments using other arthrobacter strains demonstrate that β-1,3-glucanase genes taken from various arthrobacter strains have nucleotide sequences exhibiting a large degree of homology as well as similar enzymatic activity. Consequently, the present invention includes all variants and mutant DNA sequences coding for an enzyme having substantially the same enzymatic activities an the enzyme described hereinbelow.

Cloning of the β-1,3-glucanase gene from *Oerskovia xanthineolytica*

The bacterial strain *Oerskovia xanthineolytica*, of which the β-1,3-glucanase gene used in the context of the preferred embodiment of the present invention was isolated, was obtained from Dr. Randy Schekman (University of California, Berkeley). The strain was originally *Arthrobacter luteus* strain 73-14 obtained from Yasshishi Yamamoto (Kirin Brewery, Takasaki, Gunma, Japan) and has since been reclassified by Mary Lechevalier (Rutgers University) as *Oerskovia xanthineolytica*. This strain, is described in U.S. Pat. No. 3,716,452 and may also be obtained from the American Type Culture Collection, 12301 Parklawn Drive, Rockville, Md. 20852, under accession number ATCC 21606. Since *O. xanthineolytica* and the *Arthrobacter sp.* are genetically related, it was assumed that the glucanase gene in *O. xanthineolytica* would have a similar restriction pattern as that in the *Arthrobacter sp*. The restriction map for *Arthrobacter sp.* described by Doi et al. in (1986), J. Bacteriol. 168, 1272–1276 was used as the basis for the present cloning strategy. Genomic DNA from *O. xanthineolytica* was prepared using the procedure described by Meade et al. in (1982), J. Bacteriol. 149, 114–122, and cleaved with BamHI. DNA fragments migrating at about 8.6 kb were eluted from low melting point agarose gels, cleaved with KpnI and subjected to electrophoresis in low melting point agarose gels again. The region of the gel corresponding to about 2.7 kb, which presumably contained the glucanase gene, was excised and the DNA reisolated. The resulting BamHI-KpnI fragments were cloned under the transcriptional control of the tetracycline resistance gene between the BamHI and KpnI sites of the plasmid YCp50 as described in Doi et al. supra. Transformed *E. coli* DH5a cells containing glucanase activity were detected by their ability to form a lysis zone on 2XYT plates containing 100 μg/ml ampicillin and 0.5% yeast cell wall prepared as described by Doi et al. supra. Among over 5000 transformants, as many as 3% of the colonies displayed small, but clear lysis zone surrounding the growing cells. Positive clones were later found to hybridize with plasmid pBX20 described by Doi et al. supra. One of the positive clones, designated YCpG1S, was used as the source of DNA for all subsequent studies.

DNA sequencing

Single-stranded DNA templates for sequencing by the dideoxy chain termination method described by Sanger et al. in (1977), Proc. Natl. Acad. Sci. U.S.A. 74, 5463–5467, were obtained by cloning the 2.7-kb BamHI-KpnI fragment of DNA from YCpG1S between the BamHI and KpnI sites of the plasmids pBluescript KS+ and pBluecript KS-. Two clones, one yielding the positive strand and the other the negative strand, were sequenced. Sequencing primers were synthesized based on the emerging sequence data. The primary nucleotide sequence data were aligned into a single contiguous segment using the MicroGenie DNA sequence analysis program (Beckmann).

Both strands of DNA were sequenced except for approximately 200 bp at the extreme 3' where the sequence was determined for only one strand. The sequencing strategy along with the location of the individual sequence readings and a partial restriction map are outlined in FIG. 1. In this figure, the restriction map of the 2.7 kb segment of DNA from O. xanthineolytica containing the β-1,3-glucanase gene is shown schematically. The arrows denote the extent and direction of the regions sequenced. All compressions were resequenced using 7-deaza-dGTP in the reaction mixtures to verify the sequence. The solid bar represents the open reading frame of the glucanase gene. The relevant restriction sites are as follows: A, ApaI; B, BamHI; Bg, BblII; K, KpnI; N, NcoI; P, PstI; S. SmaI.

Figure 2A:
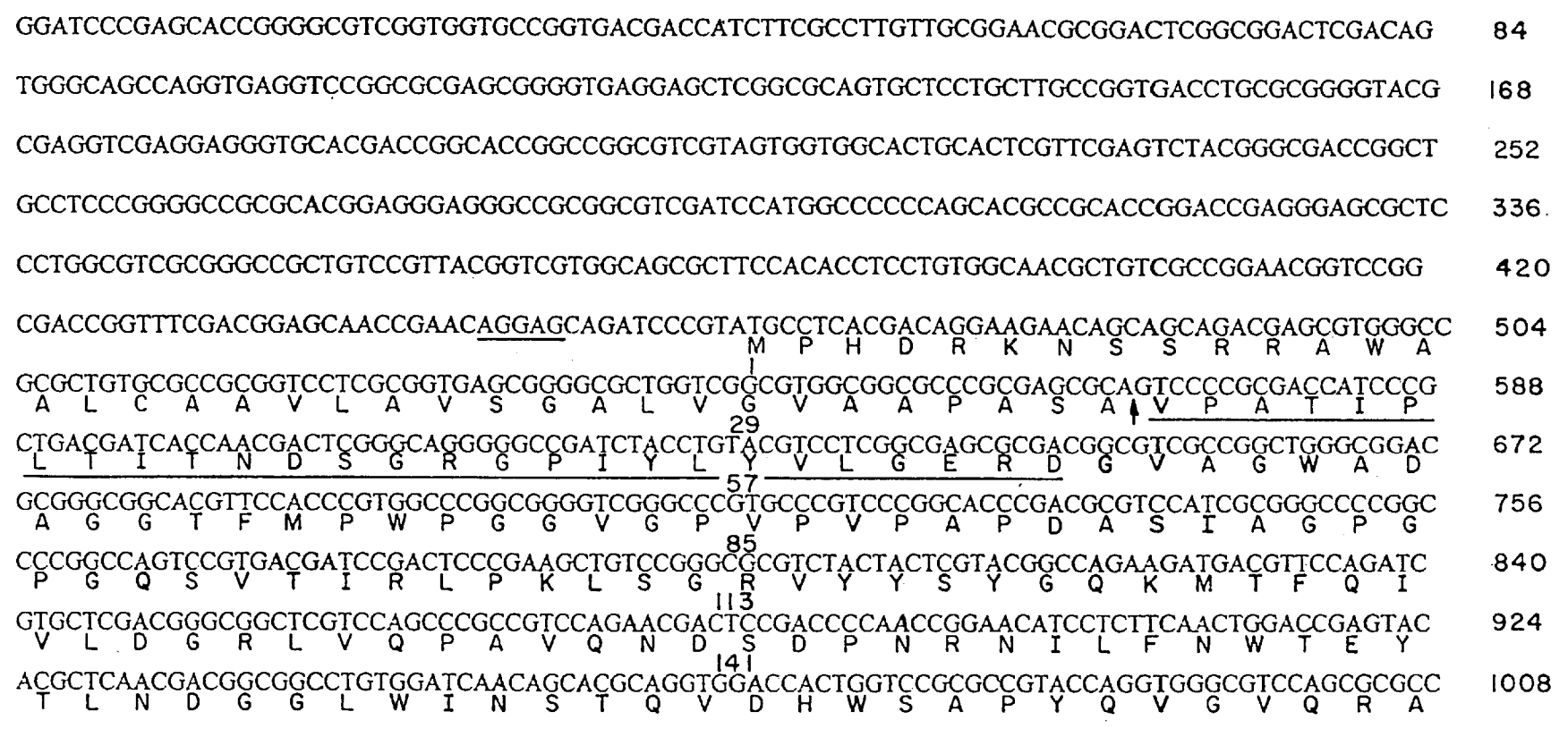

The complete nucleotide sequence of the 2.7-kb fragment of DNA containing the glucanase gene in presented in FIG. 2A–2C. In this figure, the nucleotides are numbered from the BamHI site at the 5' end of the 2.7-kb fragment of DNA. Underlined amino acids have been determined by automated Bdman sequencing of the purified native mature β-1,3-glucanase. The vertical arrow indicates the processing site of the signal peptide. Putative Shine-Dalgarno-like sequences are underlined. The palindromic sequences at the end of the open reading frame are indicated by arrows facing each other. Two stretches of repeated amino acid sequences in the carboxyterminal domain of the protein are boxed.

The sequence data show a G+C content of over 72%. Whether such a high G+C composition is a unique feature of this particular DNA fragment or a general characteristic of this organism in unclear.

The sequence data revealed the presence of two large open reading frames. One, starting at nucleotide 297 and ending at nucleotide 2045, can potentially encode a polypeptide of 583 amino acids; the other, beginning at nucleotide 463 and terminating at nucleotide 2106, predicts a protein of 548 amino acids. To determine which reading frame is actually used for the glucanase protein, the native β-1,3-glucanase protein from commercial Zymolyase preparations was purified and subjected to 27 cycles of automated Edman degradation. Comparison of the obtained sequence data with the possible amino acids deduced from the DNA sequence, revealed a perfect match with residues 37 to 63 predicted from the second open reading frame. Accordingly, the complete amino acid sequence of the glucanase deduced from this open reading frame is presented in FIG. 2A–2C.

The fact that the aminoterminus of the native protein lies at position 37 of the predicted amino acid sequence suggests that the enzyme purified from the culture medium of O. xanthineolytica is processed and that the first 36 residues constitute a signal for secretion. Computer analysis showed that this region of the protein possesses the characteristics of a signal peptide and predicted the cleavage site for processing to be between Ala36 and Val37, a location in complete agreement with the aminoterminal sequence data.

Computer scanning of the sequences upstream of the coding region could not find sequences compatible with an E. coli type of promoter. Deletion of the tetracycline promoter in the YCpG1S plasmid resulted in complete lose of ability of newly transformed cells to form lysis zone. These observations suggest that the promoter sequences in this organism are different and nonfunctional in E. coli. However, since the Shine-Dalgarno sequences of the tetracycline promoter, as present in the YCpG1S plasmid, are too far upstream of the glucanase initiation codon (nucleotide 463), it is likely that the native ribosomal binding site is being used. A possible candidate for a putative Shine-Dalgarno sequence would be the stretch of AGGAG starting at nucleotide 448, 10 nucleotides upstream of the initiator ATG. In the 3' non-coding region, there is a GC-rich 16-bp inverted repeat sequence 30 nucleotides following the terminator codon TGA. This symmetric sequence predicts a stable stem-loop structure with a free energy of about −43.2 Kcal/mol which could be a signal for termination of transcription.

Two features are worth noting in the deduced sequence of the glucanase protein. First, six out of eight cysteine residues are approximately evenly distributed within the carboxyterminal 117 amino acids as shown in FIG. 2A–2C. The other two are located nearly in the middle of the protein and are separated by 19 residues as are the other 6 (separated by 18 to 24 residues). Second, a stretch of 5 amino acids (GKCLD) close to the carboxyterminal end of the protein is repeated in its entirety. A few residues following this short repeat is a segment of 19 amino acids which also appears to be duplicated with a high degree of homology 12 residues are identical and most of the remaining differences are substitutions by amino acids with similar chemical properties. In addition, over 31% amino acid identity has been found for this region of the glucanase protein with the castor bean (Ricinus communis) agglutinin, described by Roberts et al. in J. Biol. Chem. 260, 15682–15686, another protein which binds a sugar moiety. The duplicated sequences together with the six cysteine residues in this domain may play an essential role for interaction of the β-1,3-glucanase enzyme with viable yeast cells.

Construction of the glucanase expression plasmids

Several restriction enzyme sites, including one for each of NcoI and SmaI, were inserted at the unique EcoRI site into the plasmid pOP95-15 described by Fuller et al. in (1982), Gene 19, 43–54. This construction positioned the NcoI site immediately after the EcoRI site which originally lied directly downstream of the lacUV5 promoter. The fragment of DNA extending from the NcoI site (nucleotide 295) to the SmaI site (nucleotide 2,164) was isolated from the plasmid YCpG1S, and cloned into the modified pOP95-15 vector. The NcoI site in the resulting plasmid, designating pUV5-G1S, was then destroyed by mung bean nuclease digestion to eliminate possible translation initiation from the ATG codon within the NcoI site. The EcoRI site was also destroyed by mung bean nuclease digestion. To construct the carboxyterminal deletion mutant of the glucanase enzyme, an NcoI (nucleotide 295)-SfaNI (nucleotide 1,742) fragment of DNA was isolated from YCpG1S and cloned into the modified pOP95-15 vector to generate the plasmid pUV5-G11S. This construction resulted in deletion of all nucleotides downstream of codon 431 and the introduction of 4 codons due to readthrough into the multiple cloning site in the vector.

Purification of the recombinant β-1,3-glucanase

Figure 4A:
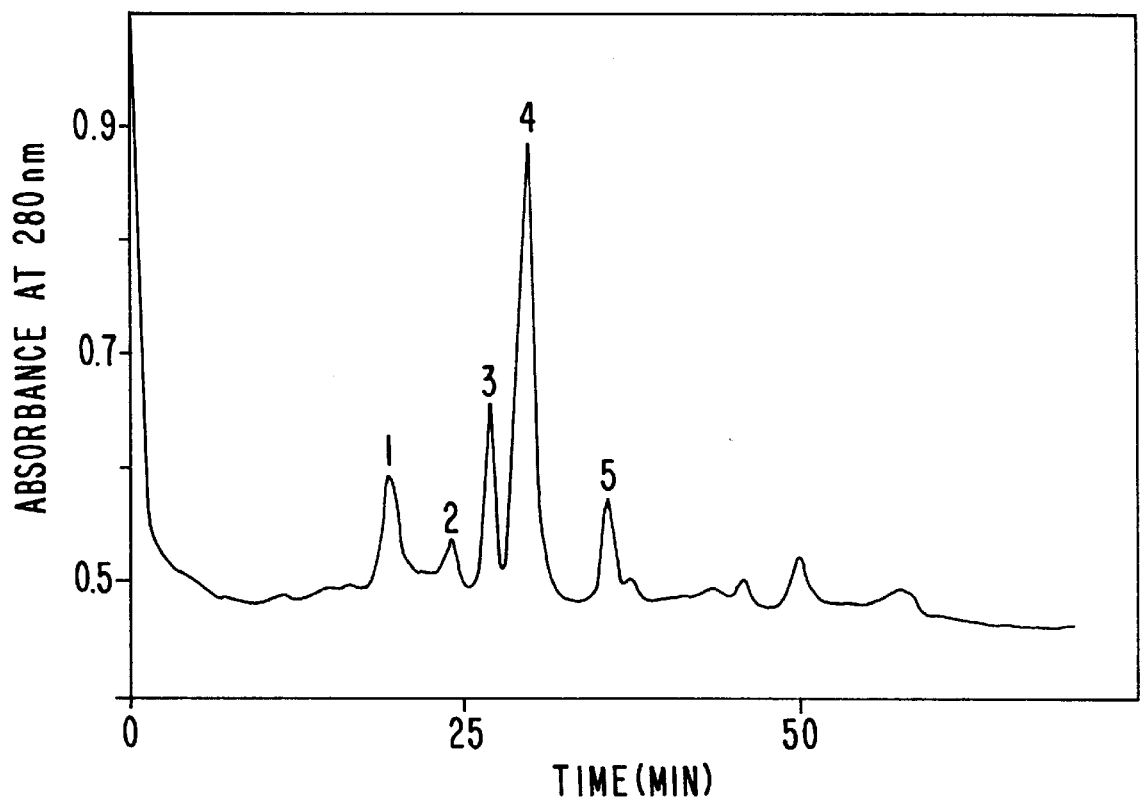
FIG. 4a represents the purification of recombinant glucanase by HPLC chromatography using an SP-5PW column.

Overnight cultures in the E. coli strain DH5α previously transformed with the glucanase expression plasmid pUV5-G1S or the mutant pUV5-G11S, following procedures known to those skilled in the art, were diluted 20-fold into 2XYT medium containing 100 µg/ml ampicillin and 1 mM IPTG and grown with vigorous shaking at 37° C. for 5–6 hours. The initial step in the isolation of the glucanase enzyme expressed in E. coli involved the preparation of osmotic shock fluid from the pUV5-G1S transformed cells. Crude glucanase preparation was thus obtained from the periplasm by subjecting the cells to osmotic shock treatment as described by Nossal et al. in (1966), J. Biol. Chem. 241, 3055–3062). Up to 1 ml of osmotic shock fluid was injected onto an HPLC system (Waters) equipped with an SP-5PW (7.5 cm×7.5 mm) cation exchange column (Waters) which had been equilibrated with buffer A (50 mM sodium acetate, pH 5.0). The column was developed at a flow rate of 1 ml/min using buffer A for 5 min followed by a 50-min linear gradient from 0 to 50 mN NaCl in buffer A. 1 ml fractions were collected. The eluent was monitored at 280 nm. Protein concentration was determined by the method of Lowry et al. which is described in (1951), J. Biol. Chem. 193, 265–275. The concentration of the purified glucanase was also measured by absorbency at 280 nm using the extinction 1 $A_{280}$-333 ng/μl derived from an analysis of the amino acid composition. Activity assays showed that the lytic activity was eluted starting at a concentration of about 28 nM sodium chloride and was localized exclusively in the major peak, which corresponds to peak 4 in FIG. 4a.

Enzyme assays

Qualitative analysis for β-1,3-glucanase activity was performed rapidly by spotting the enzyme solution onto plate& containing 1.5% Difco agar and 0.5% Zymosan A in 5 mM EDTA, pH 7.0. After incubation at 37° C. for several hours, or overnight, a clear lysis zone could be observed where glucanase activity is present. The size of the zone was found to be roughly correlated with the level of β-1,3-glucanase activity present. Quantitative determination of β-1,3-glucanase activity was performed using either Zymosan A or laminarin as a substrate. The standard assay in this laboratory employed Zymosan A as a substrate and was carried out as follows: To a suspension of Zymosan A in 50 mM Tris-HCl, pH 7.5, having an optical is density at 800 nm of 1.0, a small volume of enzyme was added and the final volume adjusted to 0.5 ml. Reactions were incubated at 37° C. in a shaking water bath for 30 min. At the end of incubation, 0.5 ml of 100 mM sodium acetate, pH 5. 0 was added and the optical density at 800 nm was read using control reactions without enzyme. One unit of β-1,3-glucanase activity is defined as a 10% decrease in optical density in 30 min. Assays using laminarin as a substrate were performed as described by Scott et al. in (1980), J. Bacteriol. 142, 414–423. The lytic activity, or ability of the enzyme to lyse viable yeast cells, was determined as described by Scott and Schekman supra, except that S. cerevisiae UC100 was used as a substrate.

The purified recombinant enzyme has a specific activity of 19.5 units/μg for lytic activity, and 35 units/μg for glucanase activity. These specific activity values are comparable to those observed for the native enzyme purified from Zymolyase under the same conditions as the recombinant one. As with the native enzyme, the recombinant glucanase has been used successfully for releasing into the culture medium of the 22-nm particles of hepatitis B surface antigen from the periplasm of yeast cells. In addition, the recombinant enzyme has proved useful in yeast transformation procedures.

Osmotic shock fluids prepared from induced cultures were examined by SDS-PAGE and visualized by staining with Coomassie Blue or immunoblotting. As shown in FIG. 3A and 3B proteins were separated in 10% acrylamide gels and stained with Coomassie blue FIG. 3A, or electrotransferred onto nitrocellulose and probed with a rabbit antiserum made against the purified native glucanase (FIG. 3B). Lane 1 represents the osmotic shock fluid from control cells harboring no glucanase gene (FIG. 3A: 5 μl; FIG. 3B: 0.5 μl). Lane 2 represents the osmotic shock fluid from pUV5-G18 transformed cells (FIG. 3A: 5 μl; FIG. 3B: 0.5 μl). Lane 3 represents the commercial Zymolyase (FIG. 3A: 1.5 μg FIG. 3B: 0.15 μg) and Lane M shows a protein molecular mass marker with sizes given in kDa.

The recombinant glucanase expressed in pUV5-G1S transformed cells is a prominent band which migrates to the same position as the authentic mature enzyme present in the commercial preparations of Zymolyase obtained from the culture medium of O. xanthineolytica. The molecular mass of the glucanase enzyme calculated from its mobility in SDS gels is approximately 57 kDa, a value consistent with the size predicted from the DNA sequence. Immunoblotting experiments showed that both the recombinant and the native mature glucanase protein immunoreacted equally well with the antiserum raised against the native mature enzyme as shown in FIG. 3B. Unlike the commercial Zymolyase preparations, which contains substantial amounts of protease activity, the recombinant glucanase is very stable and no degradation products were detected. In fact, the recombinant enzyme extracted into osmotic shock fluids and stored at 4° C. for several months showed essentially no loss of activity. Since the recombinant enzyme preparations contain no detectable protease activity, it may prove valuable for many investigational purposes.

Figure 4B:
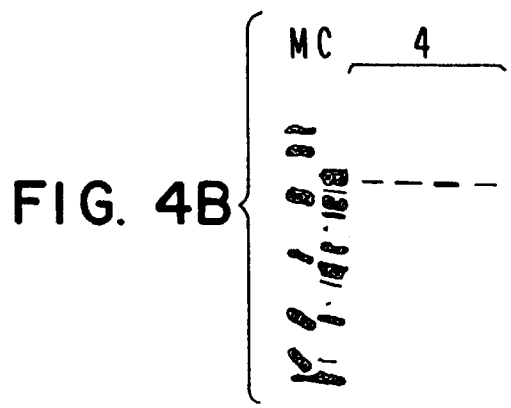
FIG. 4b represents a SDS-PAGE analysis of the glucanase fractions eluted from an SP-5PW column.

The yield of β-1,3-glucanase extracted into osmotic shock fluids from pUV5-G1S transformed cells grown in shake flasks was as high as 10 mg/liter. As mentioned earlier, this result is unexpected, especially in view of the fact that another glucanase expression plasmid in which the lacUV5 promoter was fused directly upstream of the initiator ATG codon yielded 5 times less protein. pUV5-G1S construction contains the upstream sequences (165 bp) of the native β-1,3-glucanase gene. Analysis by SDS-PAGE of the fractions purified by chromatography at and near this peak revealed the presence of single protein band of about 57 kDa in size, indicating that the recombinant enzyme has reached a high degree of purity by the single column chromatography stop as shown in FIG. 4b.

Figure 5A:
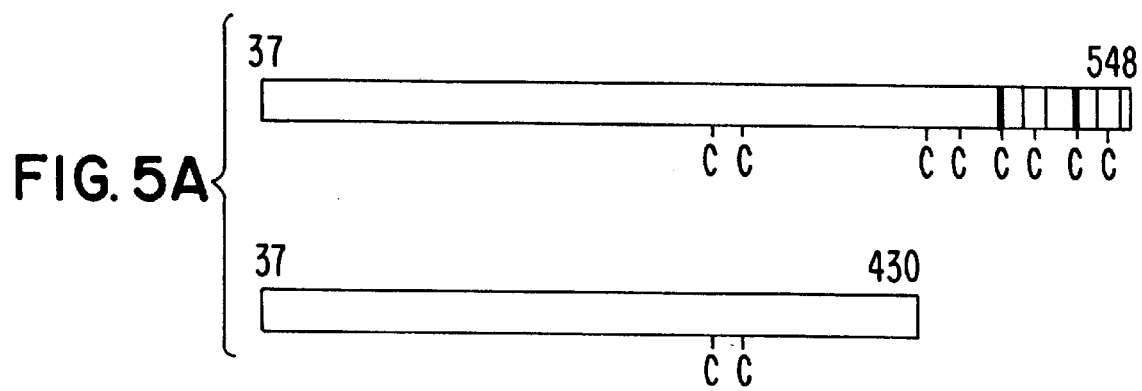
FIG. 5A and 5B represent the structure and characteristics of the wild-type and truncated glucanase proteins.
Figure 5B:

The above-discussed interesting features of the primary sequence within the carboxyterminal region of the glucanase protein, prompted the investigation of the structure-function relationship of this part of the enzyme by constructing a truncated form of the protein lacking the last 117 amino acids, including the six evenly spaced cysteines and the two duplicated segments as shown in FIG. 5A and 5B.

In FIG. 5A, the mature polypeptide of the wild-type protein (upper box) and the truncated enzyme (lower box) are schematically illustrated. The numbers above each figure are amino acid positions. The letter C marks the positions of the cysteine residues within the polypeptides. The four vertical bars depict the locations of the two stretches of repeated amino acid sequences (see FIG. 2A–2C). In FIG. 5B, a 0.5 μl aliquot of osmotic shock fluid from pUV5-G1S (lane 1) and pUV5-G11S (lane 2) transformed cells or from control cells plane 3) wax loaded onto a 10% SDS gel and immunodetected as in FIG. 3B. The numbers refer to molecular mass markers as in FIG. 3B.

Analysis of the activity of the deletion mutant by the lysis zone assay revealed that this protein produced lysis zones as large in diameter as the wild-type enzyme, though not as clear-edged. The mutant protein was also recognized by the antibody raised against the native wild-type enzyme on Western blot analysis (FIG. 5B).

Figure 6A:
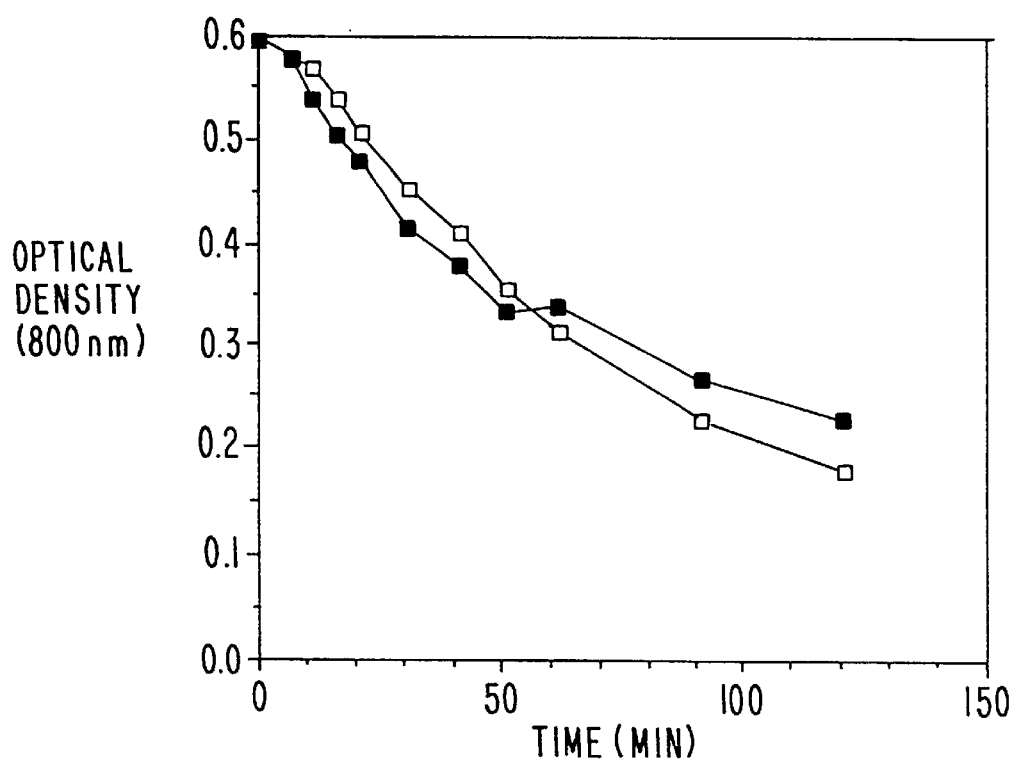
FIG. 6A and 6B represent the glucanase and lytic activity of the wild-type and the truncated glucanase enzyme.
Figure 6B:
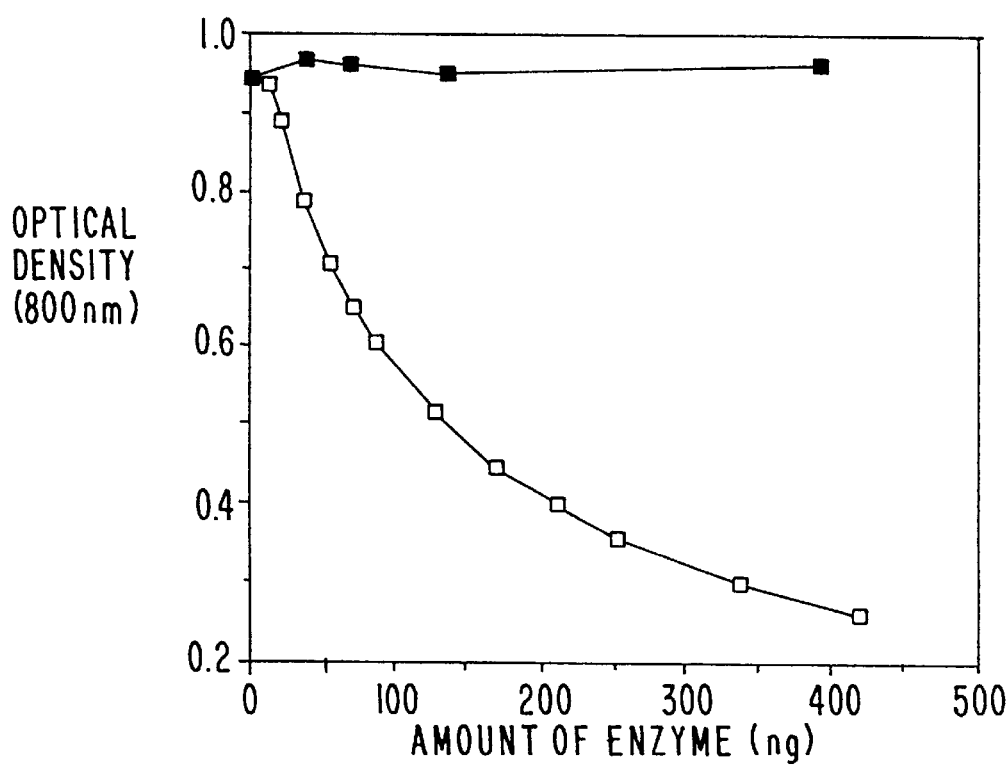

The glucanase and lytic activity of the wild-type and the truncated enzyme were also evaluated and the results are shown in FIG. 6A and 6B. In FIG. 6A, 80 ng of each enzyme was incubated with Zymosan A suspension at 37° C. as described previously and the $A_{800}$ measured at selected time intervals. In FIG. 6B, viable yeast cells were suspended in 50 mM potassium phosphate buffer, pH 7.5 and 20 mM β-mercaptoethanol at an optical density of 1.0 at 800 nm. Different amounts of purified enzymes were added and the suspension incubated at 30° C. for 30 min. At the end of incubation, the $A_{800}$ was read again. Closed squares represent the mutant enzyme and open squares represent the wild-type enzyme.

Evaluation of the kinetics for glucan digestion showed that the truncated mutant enzyme behaves in a similar time-dependent manner as does the wild-type enzyme (FIG. 6A). The calculated glucanase specific activities were around 33 and 35 units per µg, respectively. Similar results were obtained using laminarin as a substrate. Interestingly however, despite its ability to digest glucan substrates, the truncated enzyme was found to be unable to lyse viable yeast cells. As shown in FIG. 6B, while the wild-type enzyme lysed over 60% of the yeast cells at a concentration of 200 ng/ml, the mutant enzyme showed no apparent effects at concentrations as high as 400 ng/ml.

The inability of the mutant enzyme lacking the last 117 amino acids to lyse yeast cells suggests a direct role for this domain in the lytic activity of the protein. It Is possible that the two sets of duplicated residues within this domain are directly involved in binding to some repetitive structures on the yeast cell wall for anchorage and/or initiation of cell lysis. A similar hypothesis for binding has been proposed for repeated sequences in cellulase and *Staphylococcus* protein A (Uhlen et al. (1984) J. Biol. Chem. 259, 1695–1702; Beguin et al. (1985) J. Bacteriol. 162, 102–105). Since the presence of a reducing agent is required for cell lysis, it in also possible that the six cysteine residues in this domain are involved as well in the lytic activity.

The absence of lytic activity in the deletion mutant protein provides indirect support for the previous hypothesis (Doi et al. (1976) Agric. Biol. Chem. 40, 1660–1677) that the species of glucanase obtained from the supernatant of Arthrobacter cultures having little or no lytic activity were derived from the native enzyme by proteolytic cleavage. This possibility further suggests that this part of the enzyme is a relatively independent domain linked to the rest of the protein by a protease sensitive hinge structure.

Preparation of antiserum and immunoblotting

Commercial Zymolyase 100T powder was dissolved into 3 M urea and Laemmli sample buffer in which the 62.5 mM Tris-HCl, pH 6.8 was replaced by 50 mM sodium acetate, pH 5.0. The solution was boiled for 3 min and subjected to SDS-PAGE using 10% gels as described by Laemmli in (1970), Nature (London) 227, 680–685. The glucanase protein migrating at about 57 kDa was excised and the polyacrylamide gel slice was homogenized and lyophilized. The dried material was emulsified with an equal volume of complete Freund's adjuvant for the first injection, and with incomplete Freund's adjuvant for subsequent injections. Each rabbit received subcutaneously three injections (about 50 µg per injection) at three-week intervals. Animals were bled two weeks after the third injection for preparation of the antisera used in this study. Immunoblotting was carried out an described by Ey et al. in (1986), Methods Enzymol. 121, 497–509. The immunoblotting experiments were used to show that both the recombinant and the native glucanase proteins immunoreacted equally well with the antiserum raised against the native mature enzyme.

Claims to the invention follow.

We claim:

1. An isolated DNA comprising: (i) a coding region that codes for an Arthrobacter/Oerskovia enzyme with native β-1,3-glucanase activity and lytic activity, wherein said coding region is flanked contiguously by regulatory DNA regions corresponding to native β-1,3-glucanase regulatory DNA regions, and (ii) an exogenous lacUV5 promoter positioned 165 base pairs upstream of said coding region such that said promoter controls expression of said coding region.

2. An isolated DNA comprising: (i) a coding region that codes for an Arthrobacter/Oerskovia enzyme with native β-1,3-glucanase activity and lytic activity, (ii) an exogenous lacUV5 promoter positioned 165 base pairs upstream of said coding region which controls expression of said coding region, and (iii) a set of contiguous, native, regulatory DNA sequence regions which flank the 5' and 3' ends of said coding region.

* * * * *